United States Patent [19]
Bolanos et al.

[11] Patent Number: 5,471,756
[45] Date of Patent: Dec. 5, 1995

[54] LUMEN SIZERS

[75] Inventors: Henry Bolanos, East Norwalk; Richard N. Granger, Huntington; Ajit Singh, Norwalk, all of Conn.

[73] Assignee: United States Surgical Corporation, Norwalk, Conn.

[21] Appl. No.: 998,477

[22] Filed: Dec. 30, 1992

[51] Int. Cl.⁶ .......................... A61B 5/107; A61B 17/00; G01B 5/12
[52] U.S. Cl. .......................... 33/501.45; 33/512; 128/774
[58] Field of Search .................. 33/501.45, 511, 33/512; 128/774

[56] References Cited

U.S. PATENT DOCUMENTS

| | | |
|---|---|---|
| 962,171 | 6/1910 | Slotta . |
| 1,157,389 | 10/1915 | Hess ..................................... 33/501.45 |
| 3,740,779 | 6/1973 | Rubricuis . |
| 3,938,504 | 2/1976 | Dickinson, III et al. . |
| 3,993,045 | 11/1976 | Ion . |
| 4,211,241 | 7/1980 | Kaster et al. ........................... 128/774 |
| 4,226,025 | 10/1980 | Wheeler . |
| 4,240,412 | 12/1980 | James . |
| 4,517,969 | 5/1985 | Halcomb, III et al. . |
| 4,987,904 | 1/1991 | Wilson ................................... 128/774 |
| 5,042,161 | 8/1991 | Hodge ................................... 33/501.45 |

OTHER PUBLICATIONS

Information Booklet for Auto Suture S–EEA™ Sizers, c. 1988.

Primary Examiner—Christopher W. Fulton

[57] ABSTRACT

A surgical instrument for sizing the lumen of an organ is provided. The lumen sizer comprises a handle member with a projection at either end. Each projection has a substantially cylindrical sizing portion of different diameter, each diameter corresponding to the working range of a surgical instrument to be used on the organ or to the diameter of a prosthetic device to be attached to the organ. Tapered insertion regions having atraumatic tips extend from each of the substantially cylindrical sizing portions. The surgical instrument provides a fast and simple technique for measuring the lumen of an organ.

30 Claims, 4 Drawing Sheets

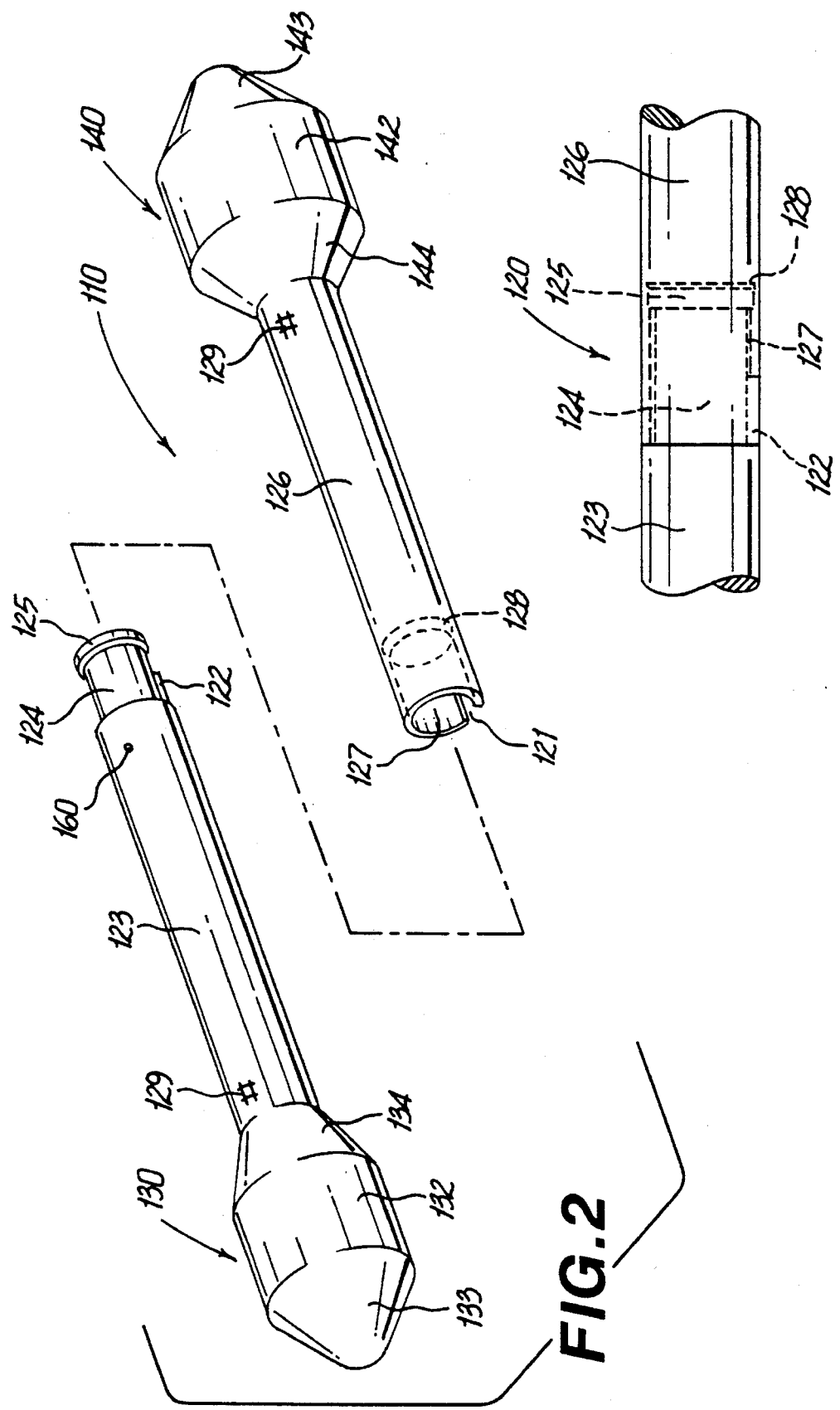

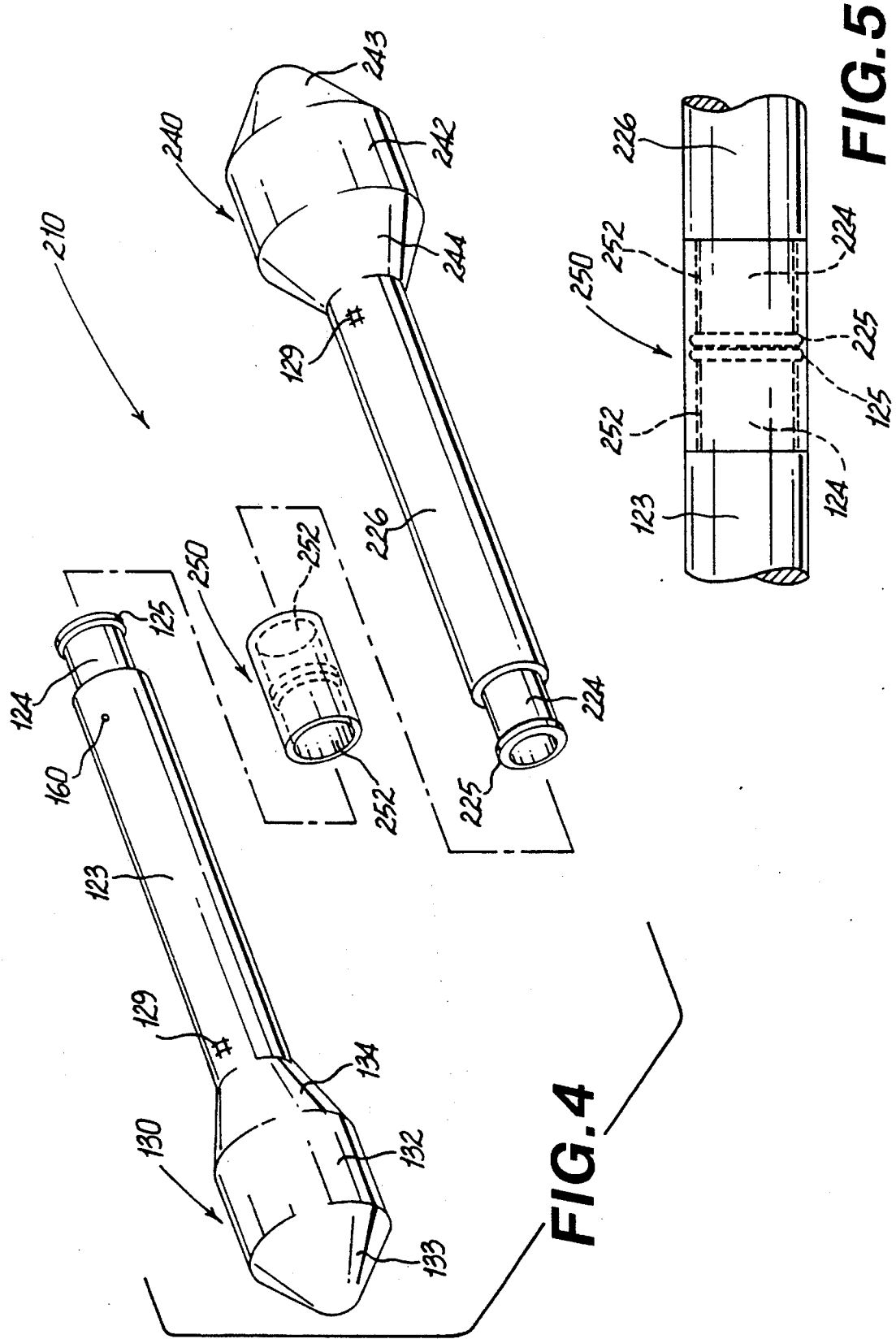

LUMEN SIZERS

BACKGROUND OF THE INVENTION

1. Field of the Invention

The present invention relates to lumen sizers, and more particularly relates to lumen sizers having a sizing projection at either end of a central hand-held portion to facilitate sizing of organs during a surgical procedure such as anastomosis.

2. Description of the Related Art

Surgical anastomosis of organs has, in recent years, increasingly involved the use of surgical staplers to join the ends of the organs. Such staplers are described in commonly-owned U.S. Pat. Nos. 5,119,983, 5,112,156, 4,752,024, and 4,603,693. Because these anastomosis staplers provide a circumferential ring of staples about the periphery of the organ wall, it is necessary to ensure that the size of the stapler head closely matches the lumen size of the organ. Thus, the lumen size must be accurately measured for selection of the appropriately-sized instrument.

Previously, devices have been introduced to size the lumens of a variety of anatomical structures during surgical procedures. U.S. Pat. No. 5,042,161 to Hodge relates to an intravascular sizing gauge having a series of sizing cylinders disposed at each end of a central holding section. Each cylinder has a diameter of a given size with cylinders having progressively decreasing diameters towards the insertion end of the instrument. The surgeon must check the instrument to read the numerical size on the gauge to ascertain correct fit of an instrument in the lumen.

U.S. Pat. No. 3,740,779 to Rubricuis relates to a surgical instrument for measuring the circumferential diameter of an orifice or mouth of a tube or duct. The instrument comprises a single cone-shaped end having a series of metered markings. The cone is inserted into the orifice until the appropriate size is reached. Like the Hodge device, the Rubricuis instrument suffers from the disadvantage that the size must be read by the surgeon to ascertain proper lumen size.

U.S. Pat. No. 3,938,504 to Dickinson, III et al. relates to a method for measuring the dimensions of the vagina, specifically, the effective diameter of the vaginal sphincter muscle of an animal. The instrument has a single, blunt-ended cone portion mounted over the end of an elongate handle. Travelling from the blunt end of the cone portion towards the handle portion, the cone portion gradually increases in diameter, reaching a maximum diameter at an intermediate ring, and then gradually decreases in diameter. This instrument has a only single insertion end and several different materials are used in the construction of the instrument. Further, the intermediate ring provides only a small surface area of maximum diameter which can lead to inaccurate measurements.

The information booklet for Auto Suture® S-EEA Sizers™ describes a reusable sizing instrument having only a single insertion end.

Thus, a need exists in the art for a surgical instrument which can quickly and accurately indicate the lumen size of an organ during surgical procedures. The need further exists for a surgical instrument having multiple sizing portions which can safely be inserted into a lumen without tissue trauma or excessive stretching of the lumen opening. Such an instrument could be used to provide an indication of lumen size to determine the size selection of a surgical instrument or prosthetic device.

SUMMARY OF THE INVENTION

The present invention overcomes the disadvantages of prior lumen sizers by providing a lumen sizer having a handle member with a projection at either end. Each projection has a substantially cylindrical sizing portion of known diameter. This known diameter corresponds to a working range of a surgical instrument to be used on the organ or to the diameter of a prosthetic device to be attached to the organ. The diameter of the substantially cylindrical sizing portion is preferably different for the projection at each end. Extending from the substantially cylindrical portion on the side opposite the handle section is a blunt, tapered insertion region having a generally conical shape. The diameter of the base of this conical section is equal to the diameter of the substantially cylindrical sizing portion. The tapered insertion region of the projection facilitates atraumatic insertion into the lumen. Towards the handle member, the substantially cylindrical sizing portion of the projection tapers down to the diameter of the handle member, forming a frustoconical joining section.

The lumen sizer can be constructed from inexpensive materials, preferably thermoplastic polymers suitable for injection molding, blow molding, or injection blow molding, thereby reducing the cost of manufacture and making the sizer suitable for single use applications. The sizer is particularly adapted for use in sizing substantially tubular organs such as the large intestine, small intestine, esophagus, vascular tissue, etc.

BRIEF DESCRIPTION OF THE DRAWINGS

FIG. 2 shows a perspective view with parts separated of a lumen sizer according to a second embodiment of the present invention.

FIG. 3 shows a side cut-away view of the assembled handle section of the lumen sizer of FIG. 2.

FIG. 4 shows a perspective view with parts separated of a lumen sizer according to a third embodiment of the present invention.

FIG. 5 shows a side cut-away view of the assembled handle section of the lumen sizer of FIG. 4.

DETAILED DESCRIPTION OF THE PREFERRED EMBODIMENTS

Figure 1:
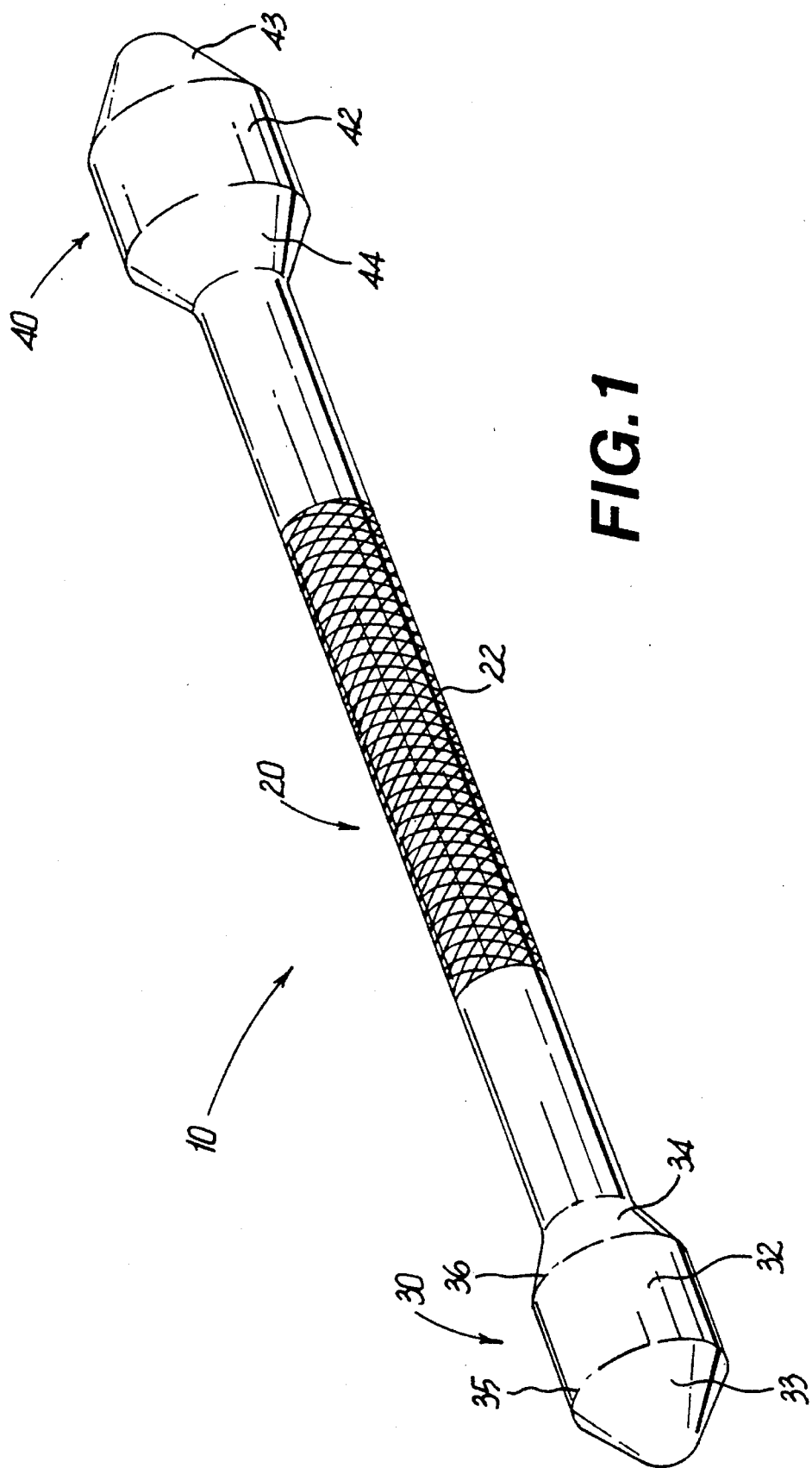
FIG. 1 shows a perspective view of a lumen sizer according to a first embodiment of the present invention.

Referring now to the drawings in detail where like reference numerals indicate like elements in each of the several views, reference is first made to FIG. 1 where a surgical instrument for measuring the size of a lumen is depicted. The instrument 10 comprises a generally cylindrical handle member 20 having a knurled or scored section 22 to facilitate gripping by the user. Extending from either end of handle member 20 are projections 30 and 40. Projection 30 has a substantially cylindrical sizing portion 32 of a known diameter. This known diameter corresponds a working range of a surgical instrument to be used on the organ or to the diameter of a prosthetic device to be attached to the organ.

Insertion portion 33 of projection 30 forms a generally conical-shaped region having a blunt, atraumatic tip. The generally conical shape of insertion portion 33 ensures insertion into the lumen of a cut organ without tissue puncturing or stretching. The base of conical insertion portion 33 joins substantially cylindrical sizing portion 32 at rounded edge 35. The diameter of the base of insertion portion 33 is substantially equal to the diameter of sizing portion 32 to further assure atraumatic insertion.

Projection 30 is joined to handle member 20 through frustoconical joining region 34. The base 36 of the frustoconical region is a circle whose diameter is substantially equal to the diameter of sizing portion 32. The region tapers down towards handle member 20 until its diameter is substantially equal to the diameter of the handle. The shape of joining region 34 is designed to allow the user to view the sizing portion 32 of the projection during insertion into the lumen. With an unobstructed view, the user can correctly ascertain whether or not the organ end fits snugly around the surface of the cylindrical sizing portion of the sizing projection.

On the opposite end of handle member 20 from projection 30 is projection 40. Projection 40 is similar to projection 30 in that is has a substantially cylindrical sizing portion 42, conical shaped insertion portion 43, and frustoconical joining region 44. However, substantially cylindrical sizing portion 42 has a diameter different from that of substantially cylindrical sizing portion 32. In use, if the lumen diameter of the organ being sized does not match the diameter of sizing portion 32 of projection 30, the surgeon merely turns the instrument around to try the other projection. Thus, the lumen size may be quickly and accurately determined without the need to select an additional instrument.

Figure 6:
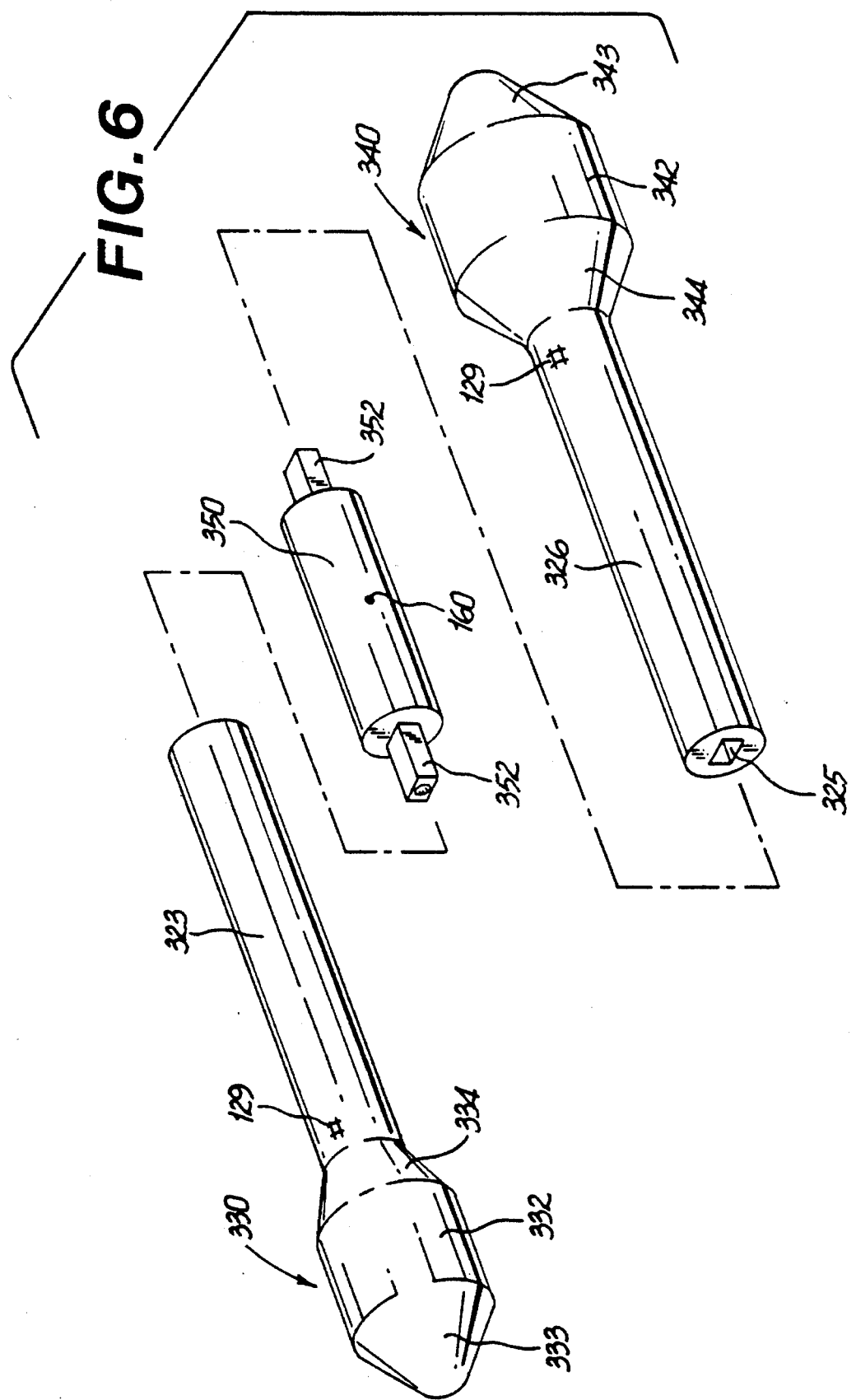
FIG. 6 shows a perspective view with the parts separated of a lumen sizer according to a fourth embodiment of the present invention.

As shown in FIGS. 2, 4, and 6 the lumen sizers of the present invention may be formed from two handle sections, each handle section having a projection monolithically formed therewith. Connection means are provided to unite the two handle sections. In FIG. 2, handle section 123 is monolithically formed with projection 130, having cylindrical sizing portion 132, conical insertion portion 133 and frustoconical joining region 134 at one end. At the opposite end, male snap fitting projection 124 having ridge 125 extends from the handle section. An optional key, 122, extends from the snap fitting projection 124 for mating with a corresponding groove to maintain alignment of the two handle sections.

To indicate to the user the size of substantially cylindrical sizing portion 132, a sizing number, element 129, is provided on the handle adjacent the sizing portion. Preferably, the sizing number corresponds to a compatible instrument or prosthetic device which may then be selected by the user for a further procedure.

A second handle section, adapted to engage handle section 123, comprises handle member 126 monolithically formed with projection 140 having substantially cylindrical sizing portion 142 (of different diameter than substantially cylindrical sizing portion 132), conical insertion portion 143, and frustoconical joining region 144. As in the first handle section, sizing number 129 is provided on the handle 126 adjacent the cylindrical sizing portion 142. At the end of handle section 126, opposite from projection 140, is female receiving portion 127 having annular receiving notch 128. Groove 121 may optionally be provided in receiving portion 127 to align with key 122 during assembly.

FIG. 3 shows the assembled handle section 120 comprising male handle section 123 engaged in female handle section 126 with ridge 125 of projection 124 engaged in annular receiving notch 128 of female receiving portion 127. Key 122 engages groove 121 such that sizing numbers 129 on each handle section are aligned in a desired configuration on the assembled sizer.

To facilitate sterilization of the lumen sizer, venting aperture 160 is provided on the handle section. Gases trapped in the interior of the sizer may be withdrawn through this aperture during sterilization.

An alternate means of joining handle sections is shown in FIGS. 4 and 5. In these Figures, handle section 123 (similar to handle section 123 of FIG. 2) and handle section 226 are joined by means of connector 250. Handle section 226, like the previous handle sections, features projection 240 monolithically formed therewith having substantially cylindrical sizing portion 242 (of a different diameter than sizing portion 132), conical insertion portion 243, and frustoconical joining region 244. At the end of handle section 226, opposite sizing projection 240, is snap fitting projection 224 having ridge 225. This projection is similar to that formed on handle section 123 and may optionally include an alignment key as in the embodiment of FIG. 2.

Connector 250 is adapted to receive both male snap fitting projections through female receptacles 252 as shown in the assembled handle of FIG. 5. It must be emphasized that the snap-fitting projections shown are merely illustrative of preferred embodiments. Any conventional procedure for joining elements as known in the art may be employed with the lumen sizers of the present invention. Such conventional joining techniques include friction-fitting, gluing, screw-type connections, welding, etc.

FIG. 6 illustrates a further means to join handle sections. In this embodiment, the handle sections 323 and 326 are joined by connector 350 having projections 352. Handle sections 323 and 326 are provided with female receiving portions 325 which engage connector projections 352 to provide a friction fit between the connector projections and the receiving portions. The shape of connector projections 352 and receiving portions 325 are such that the handles can only be assembled in the desired orientation, i.e., the orientation in which the sizing numbers, elements 129, align in the predetermined configuration. As in the previous embodiments, handle section 323 features projection 330 having substantially cylindrical sizing portion 332, substantially conical insertion portion 333, and frustoconical joining region 334; handle section 326 features projection 340 having substantially cylindrical sizing portion 342, substantially conical insertion portion 343 and frustoconical joining region 344.

The lumen sizers of the present invention readily adapt to the formation of a lumen sizing kit. In such a kit, a plurality of handle sections of the type shown in FIGS. 2, 4 or 6 is provided having cylindrical sizing portions of various diameters. Means to fasten the handle sections, integral with the handle sections as shown in FIG. 2, or as separate elements, e.g., connectors 250 and 350 shown in FIGS. 4 and 6, respectively, are provided in the kit. The user may select and assemble a pair of handle sections based upon the estimated size of the lumen to be measured. Thus, a lumen sizer custom-matched to the particular application is fabricated.

The lumen sizers of the present invention are preferably adapted to be disposable. As such, it is contemplated that inexpensive materials of construction such as polymers are used. In particular, an acrylo butudiene styrene polymer such as Magnum 2610™, available from Dow Chemical, is a suitable construction material. Each handle section may be a hollow, monolithically formed element using conventional forming techniques. Injection blow molding is a suitable fabrication method for the handles shown in FIGS. 2 and 4. In injection blow molding, a thermoplastic polymeric material is injected into a cavity and around a core rod, forming a hollow shape known as a parison. The parison, still formed on the core rod, is transferred to a blow mold, followed by injection of air into the parison through the core rod. The parison is blown against the mold walls, forming a hollow polymer object.

For the handle sections shown in FIG. 6, blow molding may be used. In blow molding, a portion of thermoplastic material is extruded and captured in a blow mold. Air is inserted into the material through a blow pin which forms the material against the mold walls. Both injection blow molding and blow molding advantageously permit inexpensive fabrication of parts to close tolerance, a desirable feature for disposable sizers.

In use, an organ having a defective section is resected. The sizer of the present invention, optionally coated with a lubricant, is inserted into the lumen of the organ. If the lumen opening snugly fits the substantially cylindrical sizing portion of the projection, the instrument or prosthetic device corresponding to the diameter of the sizing portion is selected for use with the organ. If the lumen opening loosely fits around the diameter of the sizing portion of the projection, or if the projection cannot be inserted beyond the tapered end portion, the sizing projection at the opposite end of the handle member is inserted into the lumen opening and the sizing process is repeated. In this manner, a fast and simple measurement is achieved. If neither projection provides a snug fit in the lumen opening, an additional lumen sizer is selected, the sizing portions of which have different diameters from the sizing portions of the first lumen sizer.

While the invention has been particularly shown and described with reference to the preferred embodiments, it will be understood by those skilled in the art that various modifications and changes in form and detail may be made without departing from the scope and spirit of the invention. Accordingly, such modifications are to be considered within the scope of the invention.

What is claimed is:

1. A surgical instrument for determining the size of a lumen of an organ comprising:

an elongated handle formed of hollow construction having first and second ends, the surface of said elongated handle defining a vent hole formed therethrough, said elongated handle including a first handle section monolithically formed with a first projection extending from said first end and a second handle section monolithically formed with a second projection extending from said second end, said first and second handle sections further including joining structure attachable therebetween, said joining structure including alignment guides to align said first and second handle sections in a predetermined orientation, said first and second handle sections being provided with indicia at a predetermined position, such that when said first and second handle sections are joined, the indicia are positioned at a predetermined orientation relative to each other;

said first projection including a substantially cylindrical sizing portion having a first diameter, a tapered frustoconicial portion extending distally from said substantially cylindrical sizing portion, and a joining section for uniting said substantially cylindrical sizing portion with said first end of said handle; and said second projection including a substantially cylindrical sizing portion having a second diameter, said second diameter being different from said first diameter, a tapered frustoconical portion extending distally from said substantially cylindrical sizing portion, and a joining section for uniting said substantially cylindrical sizing portion with said second end of said handle.

2. A surgical instrument for determining the size of a lumen of an organ comprising:

an elongated handle having first and second ends, said elongated handle including at least one aperture adapted to facilitate sterilization of said surgical instrument;

a first projection extending from said first end of said handle, said first projection including a substantially cylindrical sizing portion having a first diameter, a tapered frustoconical portion extending distally from said substantially cylindrical sizing portion, and a joining section for uniting said substantially cylindrical sizing portion with said first end of said handle; and a second projection extending from said second end of said handle, said second projection including a substantially cylindrical sizing portion having a second diameter, said second diameter being different from said first diameter, a tapered frustoconical portion extending distally from said substantially cylindrical sizing portion, and a joining section for uniting said substantially cylindrical sizing portion with said second end of said handle.

3. A surgical instrument according to claim 2 wherein said handle comprises a first handle section and a second handle section.

4. A surgical instrument as recited in claim 3 wherein said first handle section is monolithically formed with said first projection and said second handle section is monolithically formed with said second projection.

5. A surgical instrument as recited in claim 4 wherein said first and second handle sections further comprise joining structure to join said first and second handle sections.

6. A surgical instrument as recited in claim 5 wherein said joining structure is a friction-fit assembly.

7. A surgical instrument as recited in claim 5 wherein said joining structure is a snap-fit assembly.

8. A surgical instrument as recited in claim 5 wherein said joining structure is a first snap-fit portion on said first handle section, a second snap-fit portion on said second handle section, and connecting member adapted to engage said first and second snap-fit portions.

9. A surgical instrument as recited in claim 4 wherein said first and second handle sections are formed from a polymeric material.

10. A surgical instrument as recited in claim 9 wherein said first and second handle sections are formed by blow molding.

11. A surgical instrument as recited in claim 9 wherein said first and second handle sections are formed by injection blow molding.

12. A surgical instrument as recited in claim 2 wherein said handle includes grip enhancing structure to enhance gripping by the user.

13. A surgical instrument for determining the size of a lumen of an organ comprising:

an elongated, cylindrical handle formed of hollow construction and defining a vent hole therethrough, said handle having first and second ends;

a first projection at the first end of said handle, said first projection comprising a substantially cylindrical sizing portion having a first diameter, a tapered insertion portion having a generally conical shape and having an atraumatic tip, and a joining section having a generally frustoconical shape for uniting said substantially cylindrical sizing portion with said first end of said handle; and a second projection at said second end of said handle, said second projection comprising a substantially cylindrical sizing portion having a second diameter, said second diameter being different from said first diameter, a tapered insertion portion having a generally conical shape and having an atraumatic tip, and a joining section having a generally frustoconical shape for uniting said substantially cylindrical sizing portion with said second end of said handle.

14. A surgical instrument according to claim 13 wherein said handle comprises a first handle section and a second handle section.

15. A surgical instrument as recited in claim 14 wherein said first handle section is monolithically formed with said first projection and said second handle section is monolithically formed with said second projection.

16. A surgical instrument as recited in claim 15 wherein said first and second handle sections further comprise means for joining said first and second handle sections.

17. A surgical instrument as recited in claim 16 wherein said means for joining said first and second handle sections is a friction-fit assembly.

18. A surgical instrument as recited in claim 16 wherein said means for joining said first and second handle sections is a snap-fit assembly.

19. A surgical instrument as recited in claim 16 wherein said means for joining said first and second handle sections is a snap-fit projection on said first handle section, a second snap-fit projection on said second handle section, and a joining member adapted to engage said first and second snap-fit projections.

20. A surgical instrument as recited in claim 15 wherein said first and second handle sections are formed from a polymeric material.

21. A surgical instrument as recited in claim 20 wherein said first and second handle sections are formed by blow molding.

22. A surgical instrument as recited in claim 20 wherein said first and second handle sections are formed by injection blow molding.

23. A surgical kit for determining the size of a lumen of an organ comprising:

a plurality of handle sections, wherein said plurality of handle sections are formed of a hollow construction and include at least one surface which defines a vent hole formed therethrough, each handle section comprising an elongate gripping portion formed with a projection having a substantially cylindrical sizing portion, a frustoconical tapered insertion portion extending distally therefrom, and a joining section uniting said substantially cylindrical sizing portion with the elongate gripping portion wherein the diameter of the cylindrical sizing portion is different for each of said plurality of handle sections; and connecting means adapted to coaxially unite two handle sections to form a surgical instrument for determining the size of a lumen of an organ.

24. A surgical kit as recited in claim 23 wherein said connecting means is a friction-fit assembly.

25. A surgical kit as recited in claim 23 wherein said connecting means is a snap-fit assembly.

26. A surgical kit as recited in claim 23 wherein said connecting means is a snap-fit projection on each of said plurality of handle sections and a connector adapted to engage two snap-fit projections.

27. A surgical kit as recited in claim 23 wherein said plurality of handle sections and said connecting means are formed from a polymeric material.

28. A surgical kit as recited in claim 27 wherein said plurality of handle sections and said connecting means are formed by blow molding.

29. A surgical kit according to claim 27 wherein said plurality of handle sections and connecting means are formed by injection blow molding.

30. A surgical instrument for determining the size of a lumen comprising:

an elongated handle formed of hollow construction and defining a vent hole therethrough, said handle having a first projection at a first end and a second projection at a second end;

said first projection including a substantially cylindrical sizing portion having a first diameter, a tapered insertion portion having a generally conical shape and having an atraumatic tip; and said second projection including a substantially cylindrical sizing portion having a second diameter, said second diameter being different from said first diameter, a tapered insertion portion having a generally conical shape and having an atraumatic tip.

* * * * *